(12) United States Patent
Habibi et al.

(10) Patent No.: US 10,994,083 B1
(45) Date of Patent: May 4, 2021

(54) ELECTRONIC INHALER

(71) Applicant: Bahram Kam Habibi, Fort Lauderdale, FL (US)

(72) Inventors: Bahram Kam Habibi, Fort Lauderdale, FL (US); Iulius Vivant Dutu, Boca Raton, FL (US)

(73) Assignee: Bahram Kam Habibi, Fort Lauderdale, FL (US)

( * ) Notice: Subject to any disclaimer, the term of this patent is extended or adjusted under 35 U.S.C. 154(b) by 0 days.

(21) Appl. No.: 17/140,348

(22) Filed: Jan. 4, 2021

Related U.S. Application Data

(60) Provisional application No. 63/198,203, filed on Oct. 2, 2020.

(51) Int. Cl.
*A61M 15/00* (2006.01)

(52) U.S. Cl.
CPC ...... *A61M 15/008* (2014.02); *A61M 15/0013* (2014.02); *A61M 15/0021* (2014.02); *A61M 15/0066* (2014.02); *A61M 15/0083* (2014.02); *A61M 15/0086* (2013.01); *A61M 2202/064* (2013.01); *A61M 2205/3331* (2013.01); *A61M 2205/35* (2013.01); *A61M 2205/50* (2013.01)

(58) Field of Classification Search
CPC ............ A61M 15/008; A61M 15/0013; A61M 15/0021; A61M 15/0083; A61M 15/0086; A61M 2202/064; A61M 2205/3331; A61M 2205/35; A61M 2205/50
See application file for complete search history.

(56) References Cited

U.S. PATENT DOCUMENTS 5,002,048 A * 3/1991 Makiej, Jr. .......... A61M 15/009
128/200.23
5,007,419 A * 4/1991 Weinstein ......... A61M 15/0003
128/200.23

(Continued)

FOREIGN PATENT DOCUMENTS

| WO | WO 2007/031740 A1 | 3/2007 |
| WO | WO 2017/174588 A1 | 10/2017 |
| WO | WO 2018/200431 A1 | 11/2018 |

OTHER PUBLICATIONS

Dose Counters for MDI Inhalers, by E-Pill, website pages printed Jul. 29, 2020, https://www.epill.com/mdidosecount.html.

(Continued)

*Primary Examiner* — Timothy A Stanis
(74) *Attorney, Agent, or Firm* — Daniel S. Polley, P.A.

(57) ABSTRACT

An electronic inhaler having an embedded system and a method for precise and repeatable delivery of multiple types of medications in different forms to the pulmonary system of a human user. The inhaler can include a housing defining an internal chamber for accommodating at least two cartridges (reservoirs) containing multiple medicines in different states, and a meter reservoir compartments that can automatically provide precise doses of medicine using vacuum pressure sensors. The sensors can be in communication with the internal embedded system/electronics (microcontroller) of the inhaler and the electronics/microcontroller can be in permanent communication with a software application running on the user's smart phone or other electronic device.

25 Claims, 10 Drawing Sheets

(56) References Cited

U.S. PATENT DOCUMENTS

| | | | |
|---|---|---|---|
| 5,318,015 A * | 6/1994 | Mansson | A61M 15/0065 128/200.22 |
| 5,429,122 A | 7/1995 | Zanen et al. | |
| 6,425,392 B1 | 7/2002 | Sosiak | |
| 6,523,536 B2 * | 2/2003 | Fugelsang | A61M 15/0086 128/200.14 |
| 6,698,422 B2 | 3/2004 | Fugelsang et al. | |
| 7,219,664 B2 | 5/2007 | Ruckdeschel et al. | |
| 10,130,119 B2 | 11/2018 | Murison | |
| 10,238,821 B2 | 3/2019 | Akouka et al. | |
| 10,406,300 B2 | 9/2019 | Seguin et al. | |
| 10,449,310 B2 | 10/2019 | Jackson et al. | |
| 10,525,220 B2 | 1/2020 | Hunter et al. | |
| 10,569,034 B2 | 2/2020 | Morrison et al. | |
| 2003/0101991 A1 * | 6/2003 | Trueba | A61M 15/025 128/200.14 |
| 2003/0196660 A1 * | 10/2003 | Haveri | A61M 15/0085 128/203.12 |
| 2004/0177848 A1 | 9/2004 | Alley | |
| 2005/0274378 A1 * | 12/2005 | Bonney | A61M 15/0048 128/200.23 |
| 2006/0054165 A1 | 3/2006 | Hughes et al. | |
| 2008/0011292 A1 * | 1/2008 | Sugita | A61M 15/00 128/200.19 |
| 2008/0178872 A1 | 7/2008 | Genova et al. | |
| 2009/0064996 A1 | 3/2009 | Rosh | |
| 2014/0150785 A1 | 6/2014 | Malik et al. | |
| 2014/0202477 A1 | 7/2014 | Qi et al. | |
| 2016/0045685 A1 * | 2/2016 | Hyde | A61M 15/009 128/200.23 |
| 2016/0144141 A1 | 5/2016 | Biswas et al. | |
| 2017/0231280 A1 | 8/2017 | Anton | |
| 2019/0151577 A1 | 5/2019 | Jung et al. | |
| 2019/0158938 A1 | 5/2019 | Bowen et al. | |
| 2019/0307177 A1 | 10/2019 | Maeder et al. | |
| 2019/0351158 A1 | 11/2019 | Hansen | |
| 2020/0022416 A1 | 1/2020 | Alarcon | |
| 2020/0221778 A1 | 7/2020 | Trzecieski | |

OTHER PUBLICATIONS

Proair Digihaler, website pages printed Jul. 29, 2020, https://www.rxlist.com/proair-digihaler-drug.htm#description.

* cited by examiner

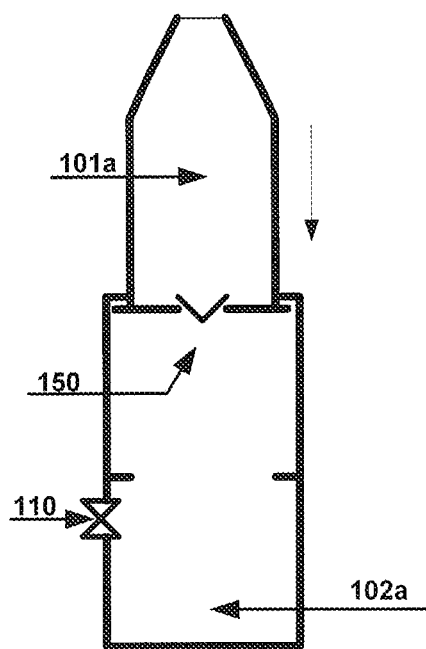
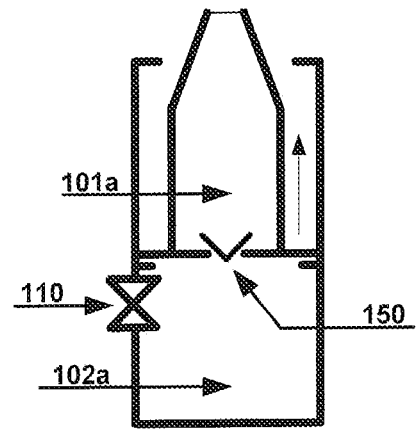
FIG.2A  FIG.2B
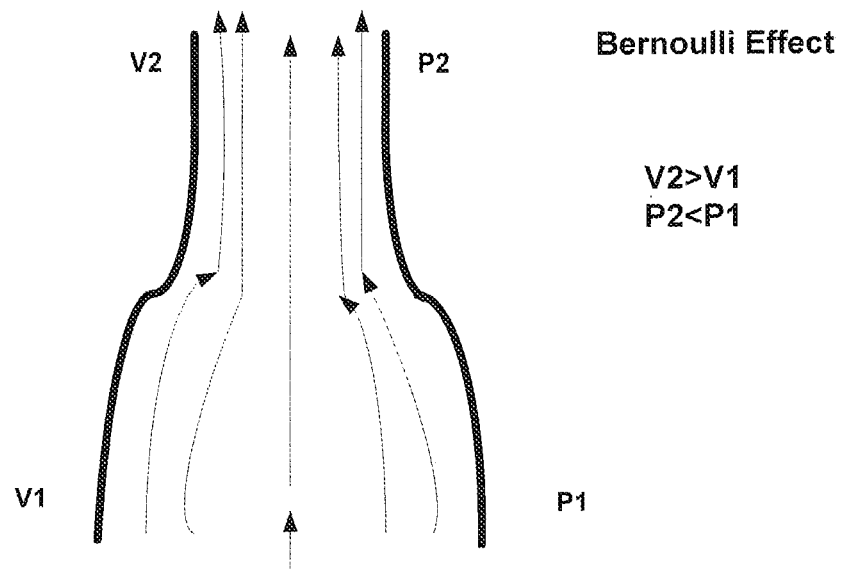
FIG.2C

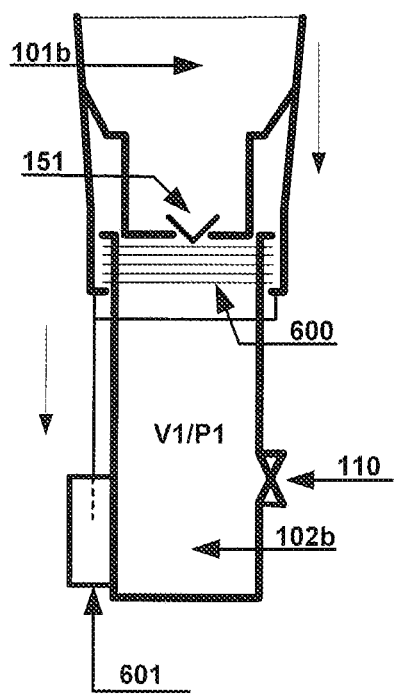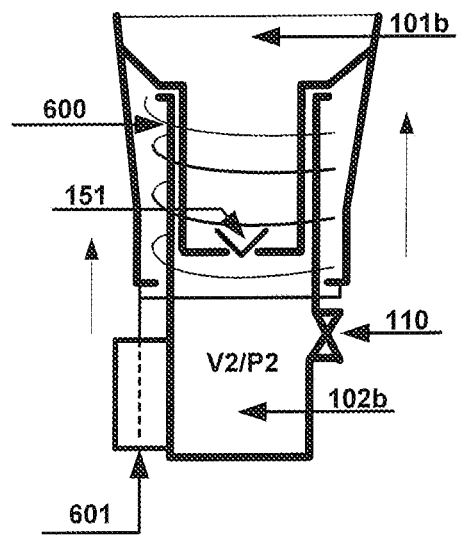
FIG. 6 A
FIG. 6 B

ELECTRONIC INHALER

This application claims the benefit of and priority to U.S. Application Ser. No. 63/198,203, filed Oct. 2, 2020, which application is incorporated by reference in its entirety for all purposes.

1. FIELD OF THE DISCLOSURE

The disclosure relates generally to inhalers and more particularly to a novel complex embedded system for an electronic inhaler which provides a method and device for precisely delivering fluids and/or powders efficiently to the pulmonary system of a patient/user while providing feedback to the patient.

2. BACKGROUND

Currently devices for treatment of respiratory diseases, such as inhalers, use aerosol delivered through inhalation creating a major challenge for providing accurate medicine delivery and dose verification based on the prescribed dose. Elements to consider for an inhaler device usually are delivery, inhalation of prescribed dose, dose verification; incorrect administering of a dose or patient misusing the dose.

For most inhaler systems today, including medicine aerosols, use large sizes of medicine molecules for their fluids and usually high speeds of fluid delivery. The high speeds of medicine delivery in such systems often does not allow the medicine to reach the bottom of the patient's lungs. Instead, because the speed is too high the medicine typically stops and is deposited in the patient's mouth and/or throat. As such, a good portion of the medicine administered with current inhalers often is lost. One approach to overcome this inconvenience is to increase the dosage amount. Increase of dosage amounts is not a favorable solution, as it potentially opens the door for unwanted side effects.

The high speed of medicine delivery mainly from the pressurized cartridge (reservoir) usually leads to a cooling effect (i.e. a condensation), and often causing the last crystallization of medicine to deposit on the exit side (i.e. mouthpiece) of the inhaler device. Where this occurs, repeated cleaning and disinfecting of the inhaler devices is required, which can lead to the end part of the inhaler mechanism to be damaged.

Accordingly, there exists a need for an inhaler device which overcomes or reduces the above-identified problems with current inhalers. As discussed below, the current disclosure addresses these problems by providing an embedded electronic inhaler which provides for an efficient mode to administer fluid and/or powder medicine, with precise dose and consistency, and while also being in electronic communication with a software app downloaded on the patient/user's smart phone or other electronic device for providing validation and feedback to patient, pharmacist, doctor, while also managing dosage types, amounts and administering times.

SUMMARY OF THE DISCLOSURE

Generally disclosed is a novel electronic inhaler having an embedded system to deliver fluid and/or powder medicines to the pulmonary system of the user. The disclosed novel inhaler may include: a housing defining an internal chamber for accommodating at least two different types of medicine cartridges, such as but not limited to, a cartridge containing powder medication and a cartridge containing a liquid/fluid medication, As another non-limiting use embodiment, two cartridges can be used with both containing powder or liquid medications, but with the medications being different from each other. Preferably, the installed cartridge(s) can be connected to or otherwise in communication with a measure reservoir compartment (MRC) for receiving a virtually exact and precise prescribed dosage amount.

Each cartridge (medicine reservoir) may have a bar code or a rewritable memory chip containing the following information: (a) the type of medication (b) the temperature of the solution, (c) density of the medication, (d) solution pressure, (e) viscosity. Once the cartridge is placed within the internal chamber of the housing the embedded system can read/detect the cartridge information, which can be displayed on the user's phone and/or other electronic device display, such as, without limitation, a computer desktop or laptop display. The displayed cartridge information can include, without limitation, medication type, administering mode and dose value. Where the cartridge medication corresponds with the prescription, the cartridge can be considered validated and can be activated by the software of the embedded system. The embedded system can be provided with electronic circuits. A microcontroller component of the electronics can read and detect all of the information and based on its algorithm can decide and provide for the best "use" output for the device. The microcontroller can be in bidirectional communication with the user's phone app, as well as in electronic communication with an electronic system of a doctor and/or/pharmacy in order to receive prescriptions/recommendations/guidelines, preferably at all times. Based on the medication density value information received from the cartridge, the microcontroller can calculate and release the prescribed dose in a virtually precise manner. Knowing the mass value of the dose prescribe and the density of the medicine, the microcontroller can be programed to calculate using the formula (volume=mass/density) an exact volume of medicine to be released in the measurement reservoir compartment (MRC).

The pressure/vacuum sensors preferably located on the mouthpiece section of the inhaler device can be in communication with the microcontroller. Once a difference in pressure and/or vacuum is sensed by the sensors, the fluid or powder medication can be released through a launch pad component. The launch pad (LP) can be part of the embedded system and can preferably connect to the medicine reservoir compartment (MRC) within a cavity area of the mouthpiece. The LP can act as a spacer and/or can move up and down within the mouthpiece for eliminating or removing deposits and/or dirt contained in the mouthpiece and for creating energy by increasing pressure in the MRC.

An actuator valve located at and/or on the end of launch pad (LP) can be controlled by microcontroller. In certain non-limiting embodiments, the actuator valve can be an electro mechanic mechanism, piezoelectric, induction and/or electromagnetic actuator. In use, the actuator valve can be designed to puncture the medication cartridge or otherwise release the prescribed dosage for the fluid or powder medication from its medication cartridge for ultimate entry into the patient's pulmonary system through use of the disclosed novel electronic inhaler.

The LP can be chosen and designed to affect the pressure and the speed (velocity) of the fluid and/or powder medication with respect to Bernoulli Effect and Coanda Effect to maximize the efficiency for delivering the fluid and/or powder medications under controlled pressure and velocity.

BRIEF DESCRIPTION OF THE DRAWINGS

The disclosure will be more clearly and easy understood based on the following drawings description:

FIG. 6 illustrate a method and alternative position for the launch pad to provide for a third source of energy of the novel inhaler in accordance with the present disclosure.

DETAILED DESCRIPTION

Figure 1:
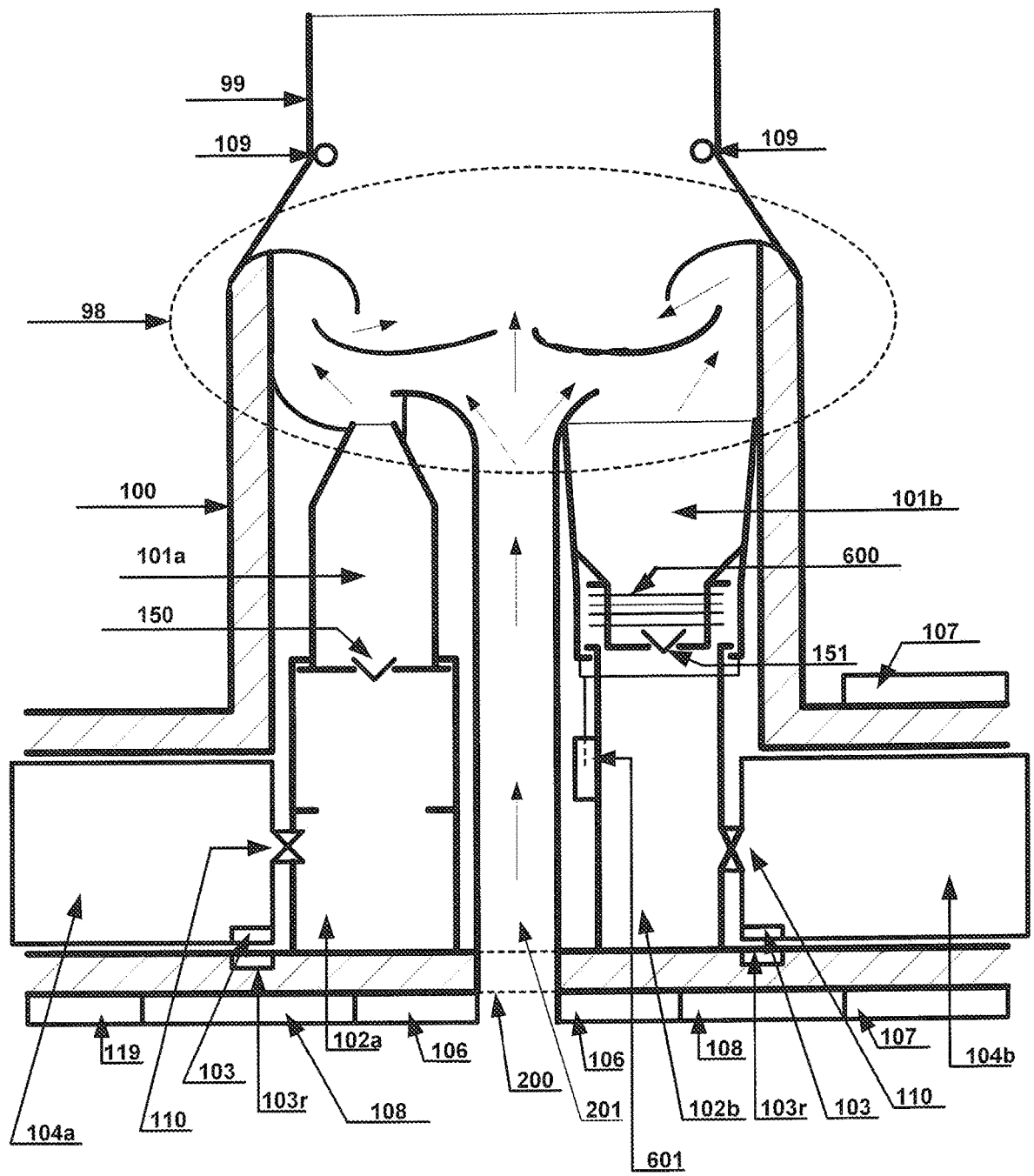
FIG. 1 is a cross sectional view of the novel electronic inhaler in accordance with the present disclosure.

The disclosed inhaler with embedded system can have a housing (100; FIG. 1), containing a mouthpiece (99; FIG. 1) having attached preferably at least two pressure/vacuum sensors (109; FIG. 1)(though such number is not considered limiting), and preferably a total of four sensors, though such is also not considered limiting. In one preferred embodiment, the housing and mouthpiece can be constructed integral or monolithically formed to form a one-piece member, though it is also within the scope of the disclosure that the housing and mouthpiece can be separate pieces that are connected together during use.

Preferably at least two different types of medication cartridges, and a preferred total of four cartridges, can be disposed or accepted within the internal chamber of the housing, though such is not considered limiting, and other number of cartridges and medication types can be used and are considered within the scope of the disclosure. The novel disclosed modular system can accommodate different types of cartridges and/or custom cartridges. Where four cartridges are received within the housing, preferably an equal number of cartridge readers (i.e. four cartridges readers) can be provided and can be in permanent communication with the microcontroller. The housing can have integrated within at least one vibrator for mixing the DPI cartridges if necessarily. One or more batteries can also be included within housing for powering at least the electronics which can also be disposed within the housing. Preferably, the electronics can have integrated wireless communication technology, such as, but not limited to, one or more of the following: Bluetooth, Zigbee, Wi-Fi, LTE, 5G, IOT, infrared, etc.). Where the batteries disposed within the housing are rechargeable, charging technology can also be provided as part of the electronics/embedded system. Alternatively or additionally to using rechargeable batteries, extended life batteries can be used for the inhaler's power source.

The software for the embedded system and/or App downloaded on the user's smart phone can be a platform application including a database and a preferred required authentication and/or authorization to access an account linked with a unique ID production tag. The communication interface between the embedded system of the inhaler and the software platform can be designed with two levels of priorities, though such number of priority levels is not considered limiting.

Level 1 can be set and/or updated/downgraded by a doctor or pharmacist. Preferably, the dosage, frequency, calendar, timing, etc. for the patient's medication can be programmed/ entered by the patient's doctor or pharmacist to avoid or reduce possible mistakes from being made. Once a medication is delivered through use of the disclosed inhaler and confirmed, the saved settings can block the particular medication from being delivered again. Preferably, delivery can only occur per the preferred doctor/pharmacist entered/ programmed schedule for the patient.

Level 2 can allow the patient to receive feedback and requests. However, preferably the patient still cannot modify the dose quantity, the frequency or schedule.

Doctors and/or pharmacists associated with the patient will preferably have access to a website or other online access where they can set the dosage, the frequency of dose administering, the type of medicine prescribed and other related information for each patient, as well as make any necessary changes or modification thereto. All of the entered information for the particular patient can be automatically communicated with or transmitted to the microcontroller of each patient's inhaler and/or the App running on each patient's smart phone, for proper dosage and scheduled settings. In case of side effects or other issues, the doctors have the ability to change the dosage and the frequency of medicine administering, as well as switching the patient's medication.

The software within the microcontroller and/or of the smart phone App can control the activation of cartridges based on confirmations and validations with the type of medication prescribed.

Figure 3:
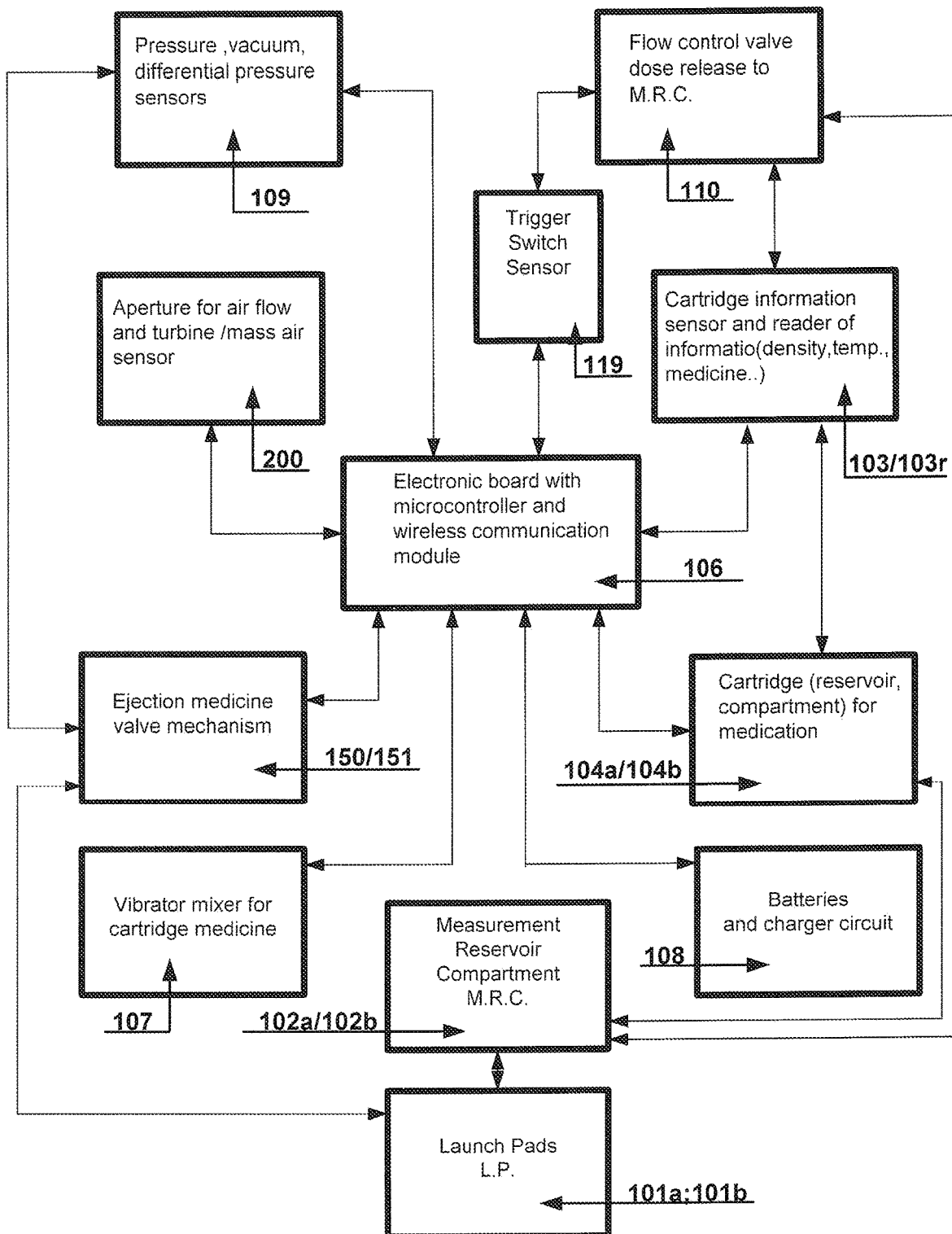
FIG. 3 is a summary block diagram of all the preferred components for the disclosed novel electronic inhaler and the preferred way they interact and communicate with each other in accordance with the present disclosure.
Figure 4:
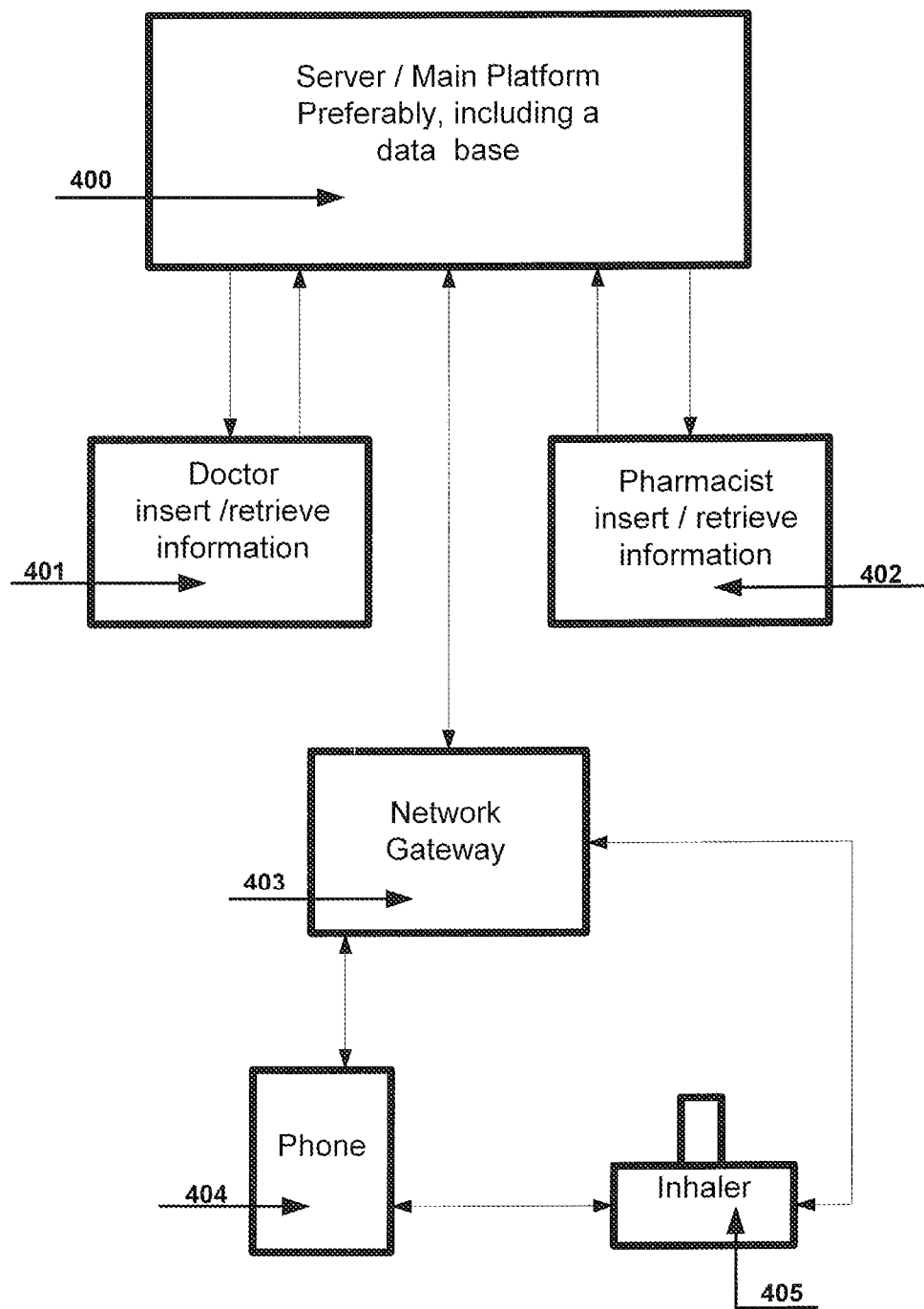
FIG. 4 is a block and flow diagram for the network and flow interconnection at different levels in accordance with the present disclosure.
Figure 5:
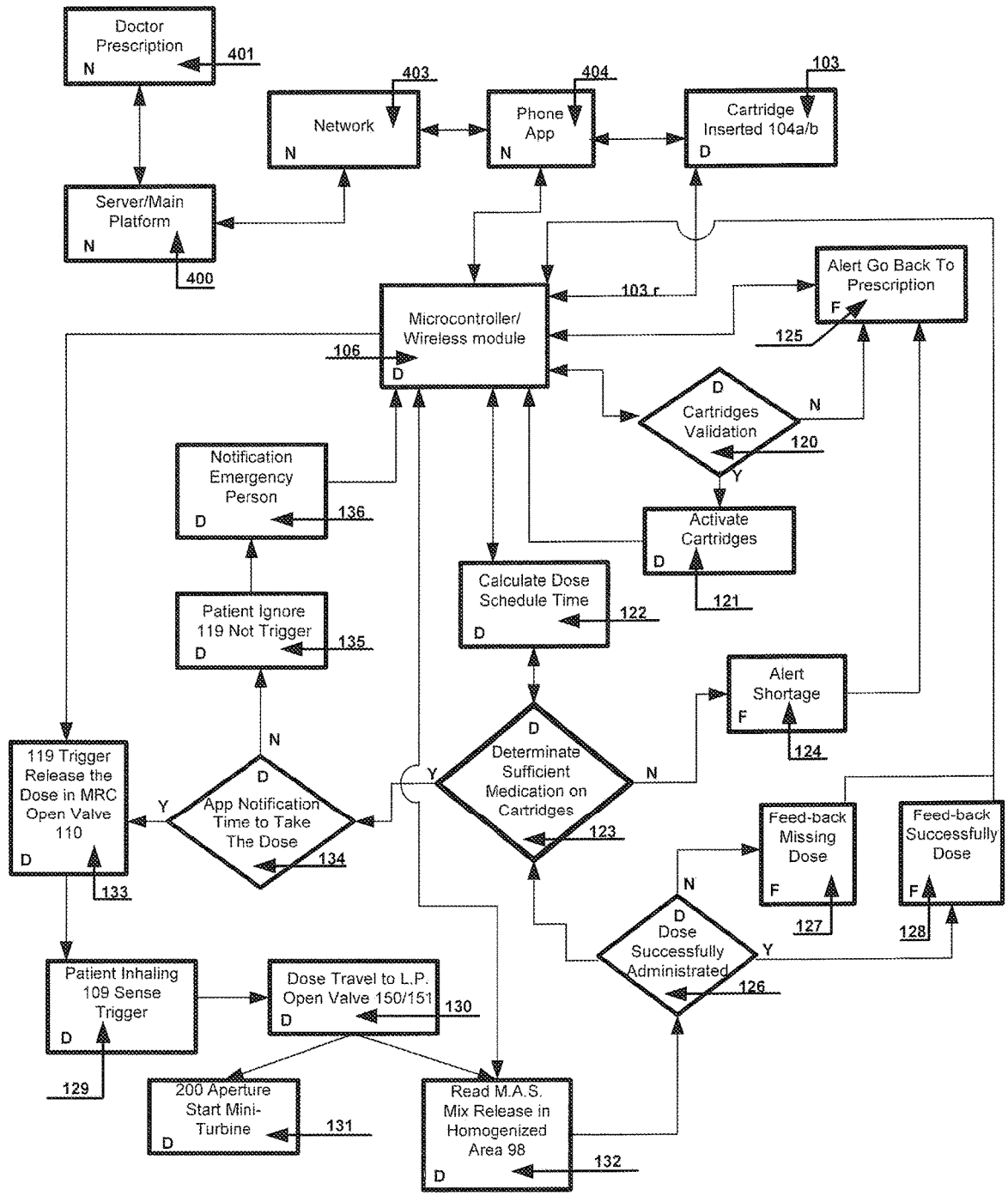
FIG. 5 is a block diagram of the logic and interconnection between the network, microcontroller and the flow interconnection of certain of the inhaler components in accordance with the present disclosure.
Figure 7:
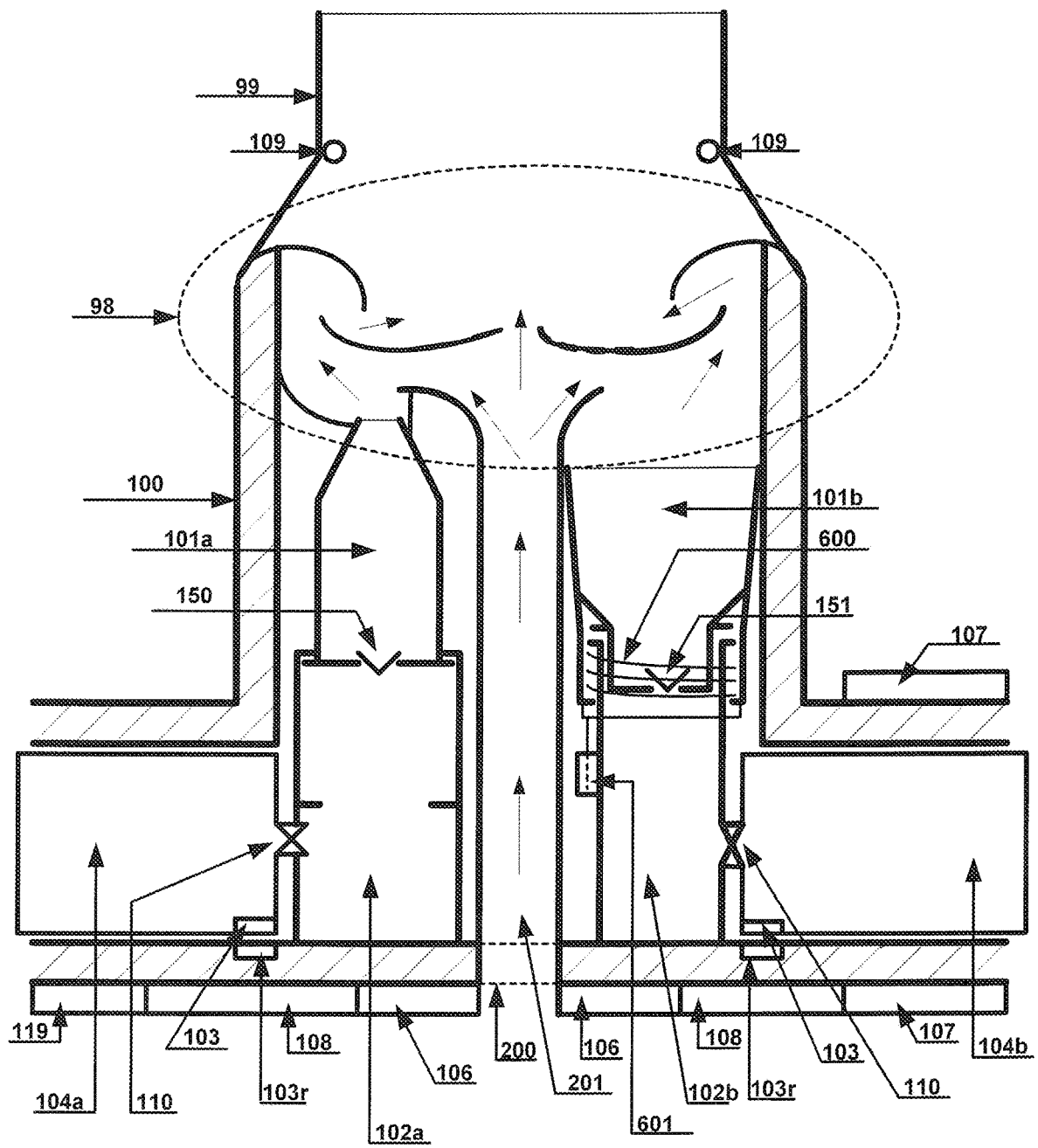
FIG. 7 is a cross sectional view of the novel electronic inhaler including the mechanism of compression in accordance with the present disclosure.

More details about the components interaction and interconnection are presented in the diagram shown in FIG. 3.

Figure 1A:
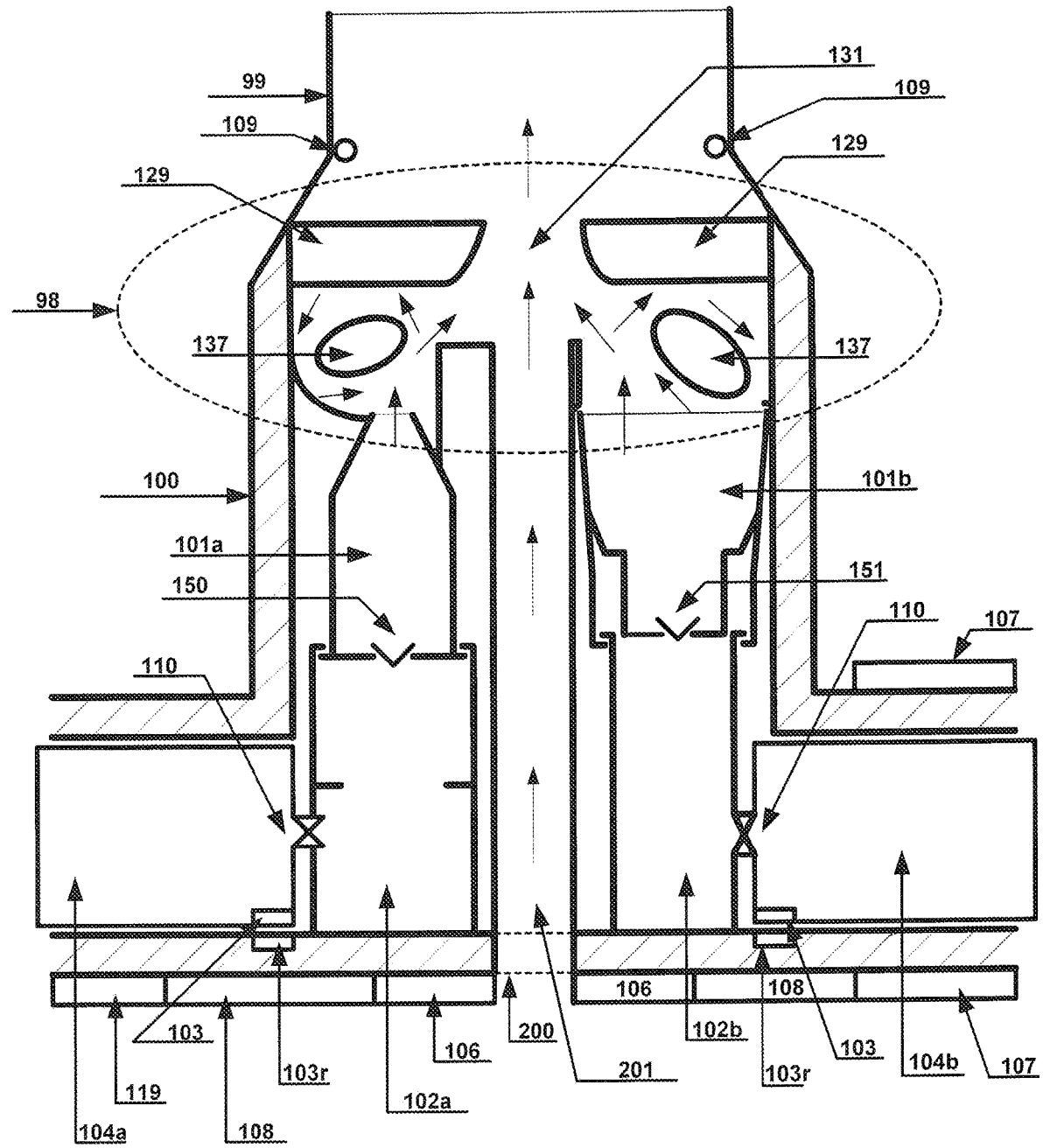
FIG. 1A is cross sectional view similar to FIG. 1 though illustrating a different mechanism for disaggregating the powder mixtures.

The disclosed novel inhaler provides an apparatus and method to properly deliver an accurate dosage of medication. The novel approach can include, without limitation, that the cartridges used (medicine reservoir, container, capsule compartment) can be provided with barcodes or IC chips (Integrate Circuit) (103) with the information of the medicine, density, and pressure fine particles fraction and temperature of fluid, as well as any other information deemed necessary for providing proper, timely and safe medication administering to the patient using the disclosed novel inhaler. Once the cartridges, regardless of type (the functionality will preferably be the same) (i.e. either Metered Dose Inhaler (MDI) or the Dry Powder Inhaler (DPI) (104*a*; 104*b*, respectively FIG. 1.)) are inserted within the housing of the device (100; FIG. 1), an electronic reader (barcode or memory chip) can be provided to extract the information from the bar code/IC chip preferably on the outside of the cartridge and sends the information to the electronics (106; FIG. 1) and specifically to microcontroller. The inhaler preferably has a Measure Reservoir Compartment (MRC), (102*a*; 102*b*; FIG. 1) in direct communication with the cartridges and Launch Pad (L.P.). The role of the MRC is to receive and stock/store an accurate dose of preferably prescribed medication/vitamins/supplements, etc. right before it is released. Knowing the dose prescribed (mass in mg or ml; knowing 1 g=1 ml) and already knowing the density of the medication, the microcontroller can calculate the volume of fluid (volume=mass: density). The algorithm of the microcontroller will open the flow control valve (110; FIG. 1 or FIG. 1A) of the cartridge for a specific time equivalent for the dose calculated and prescribed. This approach provides feedback and allows the microcontroller/downloadable App to know how much medicine is in the cartridge at any moment and also the second that a successful dose has been administered to the patient. The medicine preferably travels from the cartridge to the corresponding/associated MRC. The MRC has the correct dose and from here the fluid travels to the corresponding/associated launch pad LP and is ejected through or into a homogenized area (98; FIG. 1) where it is mixed with the airflow from aperture (200; FIG. 1) created by patient inhalation; causing the medication to enter the patient's pulmonary system through mouthpiece 99.

Valve 110 can open the cartridge (i.e. punctures, pierces and/or creates a temporary opening) stored in the associated cartridge chamber and lets a specific quantity of fluid or powder to go on (i.e. enter into) the associated MRC after the trigger switch is activated. The trigger switch can be a proximity sensor, tactile/touch sensor, on/off mouthpiece switch which can be triggered by the removal or replacement of a cover cap for the mouthpiece, or any other switch or sensor which can cause enabling of the inhaler for use upon sensing or determining that the cover cap has been removed from the mouthpiece and/or also disengage/deactivate the inhaler when the cap is returned or placed back on to the mouthpiece, etc. The valve can be flow controlled and activated by the microcontroller.

Figure 2:
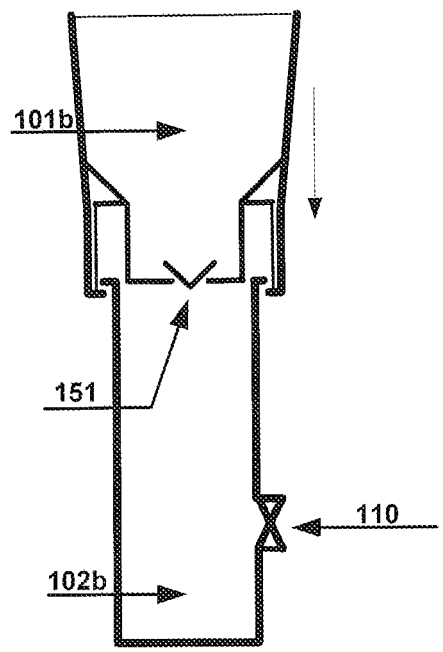
FIGS. 2A, 2B and 2C illustrate a first non-limiting embodiment for the launch pad and how the air flow characteristics are changed based on the Bernoulli effect and Coanda effect, while also showing the launch pad movement on the measurement reservoir compartment.
FIGS. 2D, 2E and 2F illustrate a second non-limiting embodiment for the launch pad and the influence of air flow velocity, pressure and trajectory with respect to the Bernoulli and Coanda effects.
FIGS. 2G and 2H another embodiment for the geometry of launch pads.
Figure 2:
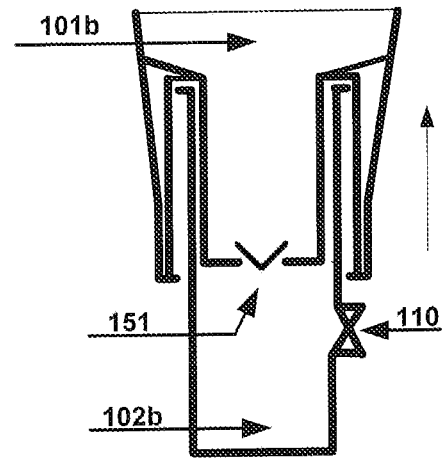
Figure 2:
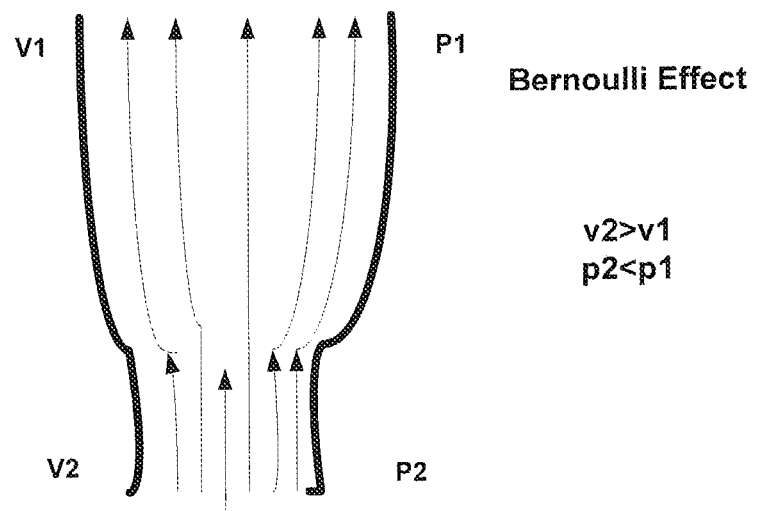
Figure 2:
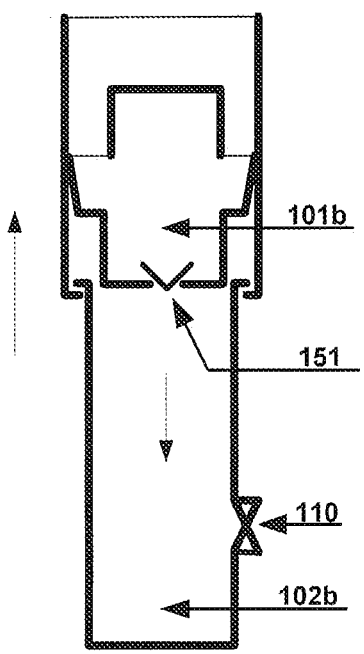
Figure 2:
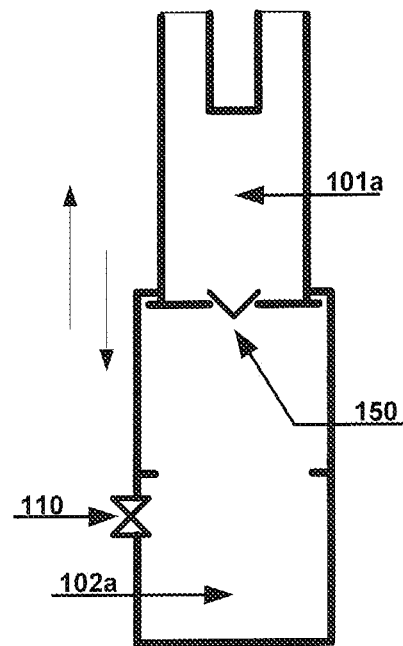

The launch pad part of the embedded system can be designed to have a reduction in pressure which occurs when the fluid speed increases and to have a reduction in speed occurring when the fluid pressure increases. This is based on the known Bernoulli equation. The launch pads have a different design (i.e. as compared to each other) based on viscosity types of medicine mix is intended to be used (101*a*; FIGS. 2A and 2B) and (101*b*; FIGS. 2E and 2F) with the specific launch pad.

The fluid traveling through the launch pads can have their velocity decreased (beneficial for eliminating any deposits to improve the flow and allowing the medicine to go deeper down into the patient's pulmonary system). At the quantum level, fluid and solid are substances for which the interaction between their constituent atoms or molecules is governed by the laws of quantum mechanics.

As a fluid stream passes through an opening in a wall, eddies appear behind the wall. The particles part of the fluid has a component direction of velocity that is larger than other component velocities, but as they interact with each other and other particles in the flow, they will move on a circular path. These processes result in a vortex effect.

In other embodiments of the disclosure, the device can be used with a variety of medicines, and drug delivery types, considering the positive effects of any fluid passing through the launch pad, and being affected by the vortex resulting in homogenizing all of the particles on the fluid and target to a path, changing the velocity and pressure.

The design of the disclosed inhaler can lead to a big improvement in the flow of particles to reach the lower side of the patient's pulmonary system and the complete bronchial tree.

Another embodiment of the disclosed device is directed to the way the fluid is influenced by passing through the launch pads directly related to pressure, velocity and trajectory (FIG. 2C and FIG. 2D).

In another embodiment, a method for drug delivery is the injector and/or ejector assembly which can allow the medication dose to be administered, and can include a valve actuator which can include, but it not limited to, piezoelectric, shape memory alloy, lab on chip, magnetic, electromagnetic, spring, valves 150 and 151 (See FIG. 1) preferably directly coupled to an aperture of an associated launch pads 101*a* and 101*b*, respectively. The valve actuators can be in direct communication with the electronics of the inhaler and the microcontroller can control when to move the valve 150 and/or 151 (i.e. the moment to open/close the valve) for efficiently administering the dose.

The inhaler can also control the on/off valve (150; 151; FIG. 1) by the microcontroller allowing the ejection of fluid on fast short sequences. The microcontroller can preferably have 5 different frequencies in memory and an algorithm can pick which frequency to use based on the size of Fine Particles Fraction (F.P.F.) dose prescribed. A higher or lower number of frequency choices above 5 frequencies can also be use and are also considered within the scope of the disclosure.

The embedded system of the inhaler may include one or more vacuum, pressure, and/or differential pressure sensors (109; FIG. 1) to engage on automatic breath actuation. The inhaler device may include an aperture 200 (See FIG. 1) at the opposite side of mouthpiece and providing a passageway and communication between aperture 200 and the homologizing area of mouthpiece 98. Though not limiting, aperture 200 can be centrally located with respect to housing 100, and preferably creates a flow of air when the process of inhalation starts. In this way the resistance is reduced resulting in easier inhaler use by children, elderly, handicapped, ill patients, etc.

Preferably, the patient can generate a peak inspiratory flow to reach a preset threshold for the microprocessor to release the medicine, through the launch pad and opening the L.P. valve(s) in the desired frequency. In accordance with embodiments of the disclosure, a Mass Air Flow Sensor, not shown, can be added to device and in direct communication with the microcontroller to increase the precision on reading the flow.

The disclosed device can be provided with several features offering a unique inhalation control taking in consideration the aerodynamics of the launch pad design and the influence at the atomic and molecular level of the fluid or powder, characterized by low airflow resistance and a smooth increase of pressure at higher flow rates during inhalation. The vortex effect created when the fluid passes through the launch pad and sequential release of fluid by the ejected mechanism and travel to the homogenized area will help to ensure a high quality medication (fluid) release. The patient and doctor can be provided with feedback or other information regarding the patient's use, so that they know that the prescribed dose of the drug was delivered, know that the necessary flow was achieved, and the medication was successfully administered to the patient. The patient and doctor can also know how many doses were taken, how much drug is left in the cartridge, when the last dose was administered, and what date/day and/or time is scheduled for the next dose administering.

The inhaler device can also help to ensure the accurate dose delivery of drug in accordance with the doctor's prescription through the use of the flow control valve (preferably placed between the cartridge and measure reservoir compartment M.R.C.) and microprocessor algorithm. The cartridges can be design for breath activated, refillable, multi-use, and propellant free operation.

The inhaler can disperse the powder mixtures into a respirable fine drug particle fraction by aerodynamic means. The aerodynamic behavior of a DPI can be affected by its design, dimension, and the geometry of the functional engineered device parts, such as the air-inlet/air-outlet, inhaler resistance, mechanisms of disaggregating powder mixtures and emptying the dose. For instance, the air-inlet size has been shown to have a significant impact on powder dispersion at different inhalation flow rates by varying the inlet jet flow turbulences and particle interaction velocity. The performance of the inhaler device can also be modified by the resistance to airflow, which can have a direct impact on the peak inspiratory flow, acceleration rate, inhaled volume to reach, and total inhalation time.

In one non-limiting embodiment, referring to FIG. 1, electronic circuit 106 is shown with a microcontroller and wireless communication module. The device may be in communication with other electronic devices via Bluetooth or other wireless technology. A power charger and batteries 108 is shown and the device can have a vibrator or vibrating mechanism 107 for keeping the fluid and/or powder mixed.

The network and communication of the disclosed inhaler device can have two levels of priority and access, though the number of levels is not considered limited to two levels.

The embedded system may have a server/main network (400; FIG. 4) where all the data is preferably recorded and stored in a database and can be accessed by the doctor (401; FIG. 4) and/or pharmacist (402; FIG. 4) to read the history of a specific patient and prescribe new/old medication, including the dosage and schedule for administering of the drug. The doctor and pharmacist can be considered part of level 1 in the network, and they can preferably have authority to change a prescription (example if patient has a side effect) or increase/decrease the dose and/or change or adjust the schedule for administering. The novel inhaler device (405; FIG. 4) may communicate directly via App running on the patient's, patient's caregiver's, etc. phone or other electronic device (i.e. portable electronic device, PC, etc. all collectively referred to as "Phone" or "phone") (404; FIG. 4). Phone 404 may access main server 400 via a network getaway 403 (FIG. 4). Inhaler device 405 may also be able to communicate directly with main server 400 via the network gateway. Phone 404 can have preloaded all the information regarding the dose and administering schedule, and notifications for the time of administering. In case the patient does not take any action after three notifications, the app can send one or more notification alerts to the persons listed as emergency contacts. The app can collect, keep and electronically send the information to main server 400 in regards with each dose taken successfully, each missed dose, how much medicine is available in the cartridge, and how many doses were missed based on the prescribed schedule and some or all of such information and any revisions/modifications based on such received information can be stored in the database associated with the server/main platform 400. In this way the patient can have feedback and information regarding the treatment, and the doctor/pharmacist can see and check at any time to see how the patient is following the schedule.

The particles needed to be administered can be based on their geometrical diameter, density, and morphology with these properties generally being manipulated during the manufacturing process. Due to inter particulate forces, mechanical interlocking, capillary, electrostatic, and van der Waals forces, micronized powders are very adhesive/cohesive, spontaneously forming agglomerates.

The extent of the partial and consequently of the combined forces is dependent on powder properties such as particle size, morphology, shape, and material, as well as on environmental factors, such as relative humidity. Since the extent of agglomeration negatively affects the fraction of the inhaled powder, which is within the respirable range, these agglomerates preferably should be effectively deagglomerated prior to or during the processes of aerosolization and inhalation.

The novel inhaler addresses deagglomeration through a homogenized or open/cavity area (collectively "homogenized") (98; FIG. 1), where the geometry of the functional device parts on the exit side of the launch pads are influenced by the airflow coming from aperture (200; FIG. 1) create a torsional vortex. In this way the aerodynamic behavior of powder particles is changed, and they may be homogenized for the processes of inhalation.

In FIG. 1 the aerodynamic effect against the fine particle fraction of mix is achieved based on cavities and chambers geometry design (based on Coanda effect), illustrated on homogenized area 98 (FIG. 1). The effect can be created by the interaction of forces of airflow from (200; FIG. 1) and powder exiting (101*a* or 101*b* FIG. 1) resulting in a torsional vortex.

In FIG. 1A a different approach of the aerodynamic behavior of the fine particle fraction is provided. This effect can be achieved based on changes on the geometry of the functional engineered device parts and the design (98; FIG. 1A). The powder exiting from launch pads (101*a* or 101*b* FIG. 1A) can be forced into the internal barriers 137 (preferably elliptical or oval in shape though not considered limiting and other shapes can be used and are considered within the scope of the disclosure) and wall barriers 129 and into opening 131 (preferably defined between wall barriers 129 and preferably centrally located) and interacting with the air flow from aperture 200 FIG. 1A will create a torsional vortex. All of this can be in total interconnection with the geometry design of the launch pads with respect to Bernoulli equation, and Coanda effect regarding aerodynamic trajectory. The vortex effect created at the quantum level, the torsional vortex created on 98 area FIG. 1, the aerodynamics of the launch pads and the sequential release (150; 151; FIG. 1A) can all be applied to the powder mixture to disaggregate the powder and homogenate the mix, making the mix ideal or otherwise improved for inhalation.

The described inhaler with embedded system can have a non-limiting advantage of utilizing a patient's inspiratory airflow as the main source of energy so that the device can be breath actuated. This inherently avoids the need to synchronize the actuation and inspiration maneuver by the patient.

In another non-limiting embodiment, a patient's inhalation (breathing pattern) can be simulated by adding a miniature turbine on the aperture (200; FIG. 1) or passageway 201 and being controlled by the microprocessor and activated at a specific airflow value. The device can have a decrease in resistance with a more efficient way to deagglomerate the particles in the fluid.

Another advantage of the inhaler with embedded system is once the cartridge device is activated and the dose is released in the measure reservoir compartment (MRC), it can ensure or at least help to reduce the chance that the mechanism does not cause an accidental release of an additional dose or additional medication.

The disclosed inhaler with embedded system may have three sources of energy. The first form of energy can be the patient's inspiratory airflow. Second, the miniature turbine, not shown in the drawings, can be located within aperture 200 or the passageway 201 associated therewith (FIG. 1) and controlled by the microprocessor and powered by the system's existing batteries. A third source of energy may be created by compression resulting from moving the launch pad down into the MRC compartment, as illustrated in FIG. 2A and FIGS. 2E and 2F.

If two different cartridges with two different medications are installed; both cartridges can be preferably validated, and after validation the cartridges can be activated, preferably based on the entered or programmed administering schedule. Based on the dose schedule, each cartridge will be preferably ON one at a time, with one exception being where medications from multiple cartridges are to be taken at the exact same time. In cases where both medications need to be administrated simultaneously, but not necessarily at the exact same time, the doctor and/or pharmacist preferably prescribes which medication should be taken first.

If the dose prescribed is larger than the volume of measurement reservoir compartment (MRC), the microcontroller can divide the dose into two equal rations and the medication will be taken in two steps, or the doctor can prescribe a cartridge with higher medicine density.

The system presented in FIG. 5, has three interconnected components:

1 network and communication with the device (N)

2 device logic functionality (D)

3 feedback and alerts (F)

Once the doctor prescribes a medication, this prescription can be written directly on the main platform for each patient (401; 400; 403; FIG. 5). Each patient preferably logs into the main platform from any PC, laptop and/or mobile electronic device for authentication and type or scan the serial number for the specific novel inhaler device that they are using. After these steps are performed, the phone application can be preferably download (from the server) and preferably the App can be preloaded with all the information regarding prescription medication type, dose value, density viscosity, temperature of medication, type of cartridges use, schedule notification time, thresholder for time for taking the medication etc. It is also within the scope of the disclosure, that the App is first downloaded and then the patient signs into the App to receive his or her specific medication/prescription information that has been preferably entered by the patient's doctor and/or pharmacists, or a hospital/clinic/urgent care facility/psychologist, etc.

At this moment in time, full communication between the device, the phone app and main platform is preferably provided (106; FIG. 5).

Once the cartridges (104*a*; 104*b*; FIG. 1) are inserted in the device, its IC memory (103 FIG. 5) can be read by a device reader (103*r*; FIG. 5) to begin the validation process (120; FIG. 5). If the cartridges don't correspond with the prescription, the doctor/pharmacist, etc. can be alerted or otherwise notified and the cartridges preferably will not be activated. If the information collected from the cartridges corresponds with the prescription, the cartridges will be validated and activated (121; FIG. 5) and considered to have an ON function from the microcontroller; calculating the dose value and schedule time (122; FIG. 5).

The next step preferably involves determining if there is enough medication in the cartridges (123; FIG. 5). If not, the doctor/pharmacists, etc. can be alerted or otherwise notified of this shortage (124; FIG. 5) and the prescription can be refilled (125; FIG. 5).

If there is a sufficient amount of medication in the cartridge, the inhaler device can be on standby waiting for the dose scheduled delivery time notification (134, FIG. 5). If the patient takes no action (135; FIG. 5) when the notification is alerted or otherwise provided, specifically after at least two notifications are ignored, the software can then automatically call or otherwise their previously designated/configured emergency contact (136; FIG. 5). All of these alerts can be in communication with and/or controlled by the microcontroller (106; FIG. 5) and a record of all notifications and any patient's actions or inactions thereto can be stored in the database. When the scheduled time is due, and the patient uses the device for inhalation, a proximity sensor can preferably engage (119; FIG. 1) (or while they are removing the cap on the mouth piece, or an on/off switch, only in the scheduled time in a threshold interval, preferably between 15 minutes to 30 minutes—though such range is not considered limiting) can open the valve (110; FIG. 1) reassessing the calculated dose in the measurement reservoir compartment (MRC) (133; FIG. 5).

When the patient starts inhaling through the device, the sensors (109; FIG. 1) preferably sense such activity and can trigger the function process of the device including causing the operation of the inhaler for medication administering to automatically start. The precise dose can be preferably already in the measurement reservoir compartment (MRC) and will travel to the launch pad (LP) by opening the valves (150; 151 FIG. 1), (130; FIG. 5) in specific sequences based on the viscosity of powder provided by the information from (103; FIG. 1) and processed by the microcontroller. Preferably simultaneously, the mini-turbine located on aperture 200 or within passageway 201 (FIG. 1) can be started/activated (131; FIG. 5) and the mass air sensor (MAS) starts sending information to the microcontroller (132; FIG. 5). The powder can be preferably released to area (98; FIG. 1), for the deagglomerating process and the homogenizing process with the air coming from aperture 200 and/or passageway 201 (FIG. 1).

A mass air sensor (MAS) will technically validate if the dose was successfully administrated (126; FIG. 5) based on the value and time of the patient's inhalation. All the readings ranging between 75% to 100%, based on the value and time recorded by patient's inhalation can be considered a successfully administrated dose (128; FIG. 5), though other ranges can be used and are also considered within the scope of the disclosure. These readings and percentages can be visually displayed on the phone app (404; FIG. 5), recorded on/stored within the database of the main platform (400; FIG. 5), and the dose can be subtracted from the previous value to accurately determinate the medication remaining in the cartridge (123; FIG. 5). If the dose is recorded as incomplete or not successfully administrated, the recording process can still subtract from the previous value. In case the patient obtains three continuous, unsuccessful dose recordings, the server can send a notification to the doctor and emergency contacts. Other high or lower numbers of continuous unsuccessful dose recordings can also be used and are considered within the scope of the disclosure.

The device housing (100; FIG. 1) may accommodate cartridges in different sizes; small, medium, and large as one non-limiting example.

The entire administration dose process may be monitored in real time on displays of the phone or PC devices, including the feedback and/or notification.

In some circumstances, patients may have to take five or more different medications with some in dry powder and/or some in liquid form. The disclosed inhaler with embedded system will be able to provide the possibility of using multiple cartridges with either or both dry powder or liquid form. The device has the capacity of holding four different medications in different forms in one embodiment and in another embodiment two different cartridges can be provided within the device, though the number of medication cartridges are not considered limited to any specific number of cartridges.

As a non-limiting example, two cartridges may have different medications in different forms and be inserted in device (104a; FIG. 1), Metered Dose Inhaler (MDI), and (104b; FIG. 1) the Dry Powder Inhaler (DPI). In this non-limiting example, the general process for use can include, without limitation:
(1) the cartridges can be validated based on the prescription for the patient;
(2) the cartridges are activated; and
(3) calculating the dose for each cartridge and schedule the time for notifications based on the patient's prescription for each medication.

During the scheduled time, a notification can be sent to the phone, watch, pager, pc device etc. This notification can be for a specific medication, for instance, for the MDI (104a; FIG. 1). When the patient obtains the device in hand to perform the dose administration, the (119; FIG. 1) sensor will trigger and only cartridge (104a; FIG. 1) will be active ON (all others will preferably be in an OFF state). The opening of valve 110 (FIG. 1) will release the calculated dose from the cartridge to MRC. This process can be preferably quick, automatic, and occurs right before the patient starts the inhalation.

Patient inhalation will be read or otherwise sensed by sensor(s) 109 (FIG. 1), and will automatically and simultaneously trigger or otherwise start the following (i) open valve 150 (FIG. 1) at a specific sequenced rate, allowing medication traveling from MRC (102a; FIG. 1) to LP (101a; FIG. 1); (ii) preferably start mini-turbine (when provided) located at aperture 200 or passageway 201 (FIG. 1), (iii) start reading the MAS, and (iv) releasing the measured dose in homogenized area (98; FIG. 1).

When a new notification is received for different cartridges, for instance, the DPI (104b; FIG. 1) only (104b; FIG. 1) will preferably be active ON and the process will be similar to the one described above.

Each cartridge can preferably be individually active ON one at a time, based on the prescription dose administrated time schedule.

The disclosed novel inhaler device can be modular with detachable and interchange mouthpiece. In one non-limiting embodiment, to clean the device and eliminate any interaction between different medicine and/or deposits inside inhaler, a cleaning cartridge can be provided which will have a specific code and once is place on the device the microprocessor can automatically start the cleaning process A third source of energy may be created by compression resulting from moving the launch pad down into the MRC compartment, as illustrated in FIGS. 2A, 2B and 2C, FIGS. 2D, 2E and 2F, FIG. 6, FIG. 1 and FIG. 7.

The movement of LP (101b) down on MRC 102b), will create a compression and, specially for dry powder DPI, can provide for improved patient inhalation. Often for DPI, the patient is instructed to take a fast inhalation or maybe two or three repetitive hard inhalations. The novel embedded device of the inhaler described herein can create a compression, increasing the pressure in MRC (102b), which in addition to gravity (refers to the position of inhaler in use and the placement position of the cartridge, applying gravitational force to medication) can increase the pressure of medicine delivery simultaneous with the Bernoulli effect created on the LP (102b). Thus, pressure and velocity can be controlled, allowing the patient to not make any efforts (or reducing the patient's involvement) for the inhalation process. Furthermore, the patient doesn't require a learning process for using two different types of inhalers (i.e. 1. liquid and 2. dry form medication).

Boyle's law is applicable to human breathing. To breathe in, one expands their rib cage to increase its volume so that the pressure inside their lungs can decrease. Once the pressure inside the lungs becomes lower than the atmospheric pressure, air molecules are able to rush in through the person's nostrils. Similarly, to breathe out, one must contract thei rib cage to decrease its volume so that the pressure inside their lungs can become greater. Once the pressure inside the lungs becomes greater than the atmospheric pressure, air molecules are able to rush out through their nostrils. The pressure (P) of gas is inversely proportional to the volume (V) of gas. This means that as one hold's temperature (T) and amount (n) of fluid constant (same), as the pressure of gas molecules increase, the volume of gas molecules decreases. $P=K/V$ FIG. 6 illustrates the LP being positioned further down with respect to the housing and MRC. One non-limiting embodiment for positioning the LP as seen in FIG. 6 includes using a spring (600) that can be contracted and a miniature electromagnet (601) having a shaft that can be extended when the inhaler is not in use. When the medication is in MRC (102B) the microcontroller can activate the electromagnet (601) causing the shaft of the electromagnet to retract which causes spring (600) to expand and pushing down LP (101b) further down or into MRC (102B). In a non-limiting alternative embodiment, spring 600 can be removed where a more powerful or stronger pulling force electromagnet (601) is provided that can consume more energy. The movement of the LP down to the MRC can be made with other components, such as, without limitation, magnetic components, etc. like magnetic etc. With reference to FIG. 6, application of Boyle's law yields $P_1V_1=P_2V_2$; $P_1<P_2$ and $V_1>V_2$ (with P=pressure and V=volume).

Indications can be made by patient physician where medications are delivered to patient's respiratory system via inhalation device. Primary use cases can be respiratory diseases such as, without limitation, Asthma and COPD. Other extended or intended use can be medications for Diabetes, cancer, neurological disorders, neurodegenerative disorders, immunological disorders, and other diseases through which future research and development deemed to have more efficacy and potency through delivery by inhalation One non-limiting advantage of the disclosed electronic inhaler having an embedded system is the airflow, which can serve as the main source of energy. The inhaler can be preferably breath actuated, which can inherently avoid the need for the user/patient to synchronize his or her actuation and inspiration maneuver/movements.

Another non-limiting advantage of the disclosed electronic inhaler having an embedded system is a relatively low air-flow resistance making the inhaler easy to be used by young children and the elderly.

Other non-limiting advantages include:
a. Easy to handle;
b. Accurate dosage counter;
c. Minimizes deposits;
d. Improve the flow of particles into the entire patient/user's respiratory system; and
e. Feedback to patient, doctor/pharmacist regarding the dose being successfully administered, scheduled, etc.

Additional non-limiting features, benefits and/or advantages of the disclosed novel inhaler include:

1. The inhaler can be designed to accommodate and receive both dry powder and liquid/spray medications at the same time, with each medication cartridge/cylinder being received within the inhaler's chamber and each having its own launch pads. Each launch pad can be automated upon user inhalation to move forward into the mouthpiece during inhalation and retract back to its original position once the prescribed amount of drug has been delivered. This action helps to prevent or reduce drug residuals left in the mouthpiece.
2. In view of the size of the receiving chambers, the cartridges can come in preferably three (though not limiting) different sizes, small, medium, and large. The size of the cartridge needed can depend of the quantity of drugs and dosage amount/duration based on the prescription.
3. The cartridges can have sensors to communicate to the microprocessor and/or software app the amount of medicine available after each dosage has been taken by the user. The software app can also be programmed to automatically send alerts to the user's doctor and/or pharmacy when the software app learns from the received sensor information that the remaining drug level within the cartridge correlates to 50% use and 75% usage (though the range is not considered limiting) so that more medication can be ordered.
4. The user's doctor can be provided with the ability to increase or decrease the dosage amount as needed simply by logging in to the software. The software can communicate with the user's app and/or directly with the microprocessor in the inhaler to make the dosage adjustment.
5. Can allow for elimination of the use of spacers in the inhaler delivery system.
6. Three (though not limiting) different thrust levels based on patient's ability to inhale.
7. An inhalation test can be performed with no cartridges in the device. This information can be used for calibrating and calculations when setting up the inhaler for automated thrust level. Using the information from the inhalation test, the inhaler can be set up with a thrust level that best delivers the medicine to the user's lungs.
8. The inhaler provides for an efficient mode to administer fluid and/or powder medicine and allows for precise dose administration and consistency.
9. The design of the inhaler allows for efficient delivery of fluid and/or powder medication under controlled pressure and velocity.
10. The delivery of the medication can be on fast short sequences preferably based on five different frequencies (though not limiting) that can be chosen in relation with fluid density.
11. The design provides for unique inhalation control using the aerodynamics of the launch pad design and the influence at the atomic and molecular levels of the fluid, characterized by low airflow resistance and a smooth increase of pressure at higher flow rates during inhalation.
12. The design provides for a Vortex effect to be created when the fluid passes through the launch pad and based on the chosen frequency for the sequence delivery of the fluid.
13. The inhaler addresses deagglomeration by incorporating a homogenized area. The aerodynamic effect against the fluid mix can be achieved using cavities and the chamber's geometry; resulting in a torsional vortex being created in two different designs.
14. The inhaler can be provided with three sources of energy; a) patient inspiratory airflow; b) airflow from a miniature turbine preferably powered by one or more batteries; and (c) compression from moving the launch pad down into the measured reservoir compartment of the inhaler.
15. The inhaler delivers the medication by proximity sensor controlled by the inhaler's microprocessor.

The disclosed novel inhaler design addresses or reduces the following limitations/problems with current inhalers:

1. The inhaler is relatively easy to use by young children and the elderly as compared to existing inhalers. Additionally, the patient is not required to perform any synchronization between their breath and activation/release of the medication (i.e. pressing of any button).

2. The inhaler allows for the delivered medication to preferably go down on the low side of the user's lungs and thus eliminating and/or significantly reducing the deposit of medication on the user's mouth and/or the cooling effect found with existing inhalers.

3. The inhaler provides for a more precise dose amount of drug administering.

4. Through the algorithm/software and intelligence, the inhaler helps to eliminate the possibility of the user repeating taken the same dose.

5. The inhaler preferably provides for live feedback for the patient and doctor, and in certain situations also with the user's pharmacy.

6. The inhaler can be used for liquid and powder medications, with both types of medication cartridges being able to be housed within the inhaler at the same time.

7. Given that the same inhaler can be used for both liquid and powder medications, the novel disclosed inhaler design eliminates the need for the patient/user who needs to take a liquid medication and a powder medication to have to learn to operate two or more different devices, with each inhaler having different operating instructions.

8. No critical orientation for the dry powder cartridge is required with use of the novel disclosed inhaler.

The disclosed electronic inhaler having an embedded system may include the following components as shown in the drawings with the following reference numerals: (as in FIG. 1 and FIG. 1A)

100—inhaler housing:

104*a* and 104*b*—cartridges medicine reservoirs, containers, capsule compartments

103—cartridge information sensors (i.e. memory IC located on the cartridge)

103r—sensors for reading cartridge information preferably connected to microcontroller and located on the device house.
102a and 102b—measuring reservoir compartments ("MRC").
101a and 101b—launch pads ("LP")
150 and 151—injection/ejection mechanism valves
110—flow control valves
106—electronic board with microcontroller and wireless communication module
107—vibrator mixer for medicine
108—batteries and charger circuit
200—aperture airflow, turbine, mass air sensor
201—air passageway
109—pressure, vacuum, differential pressure sensors
119—trigger switch sensor
99—mouthpiece
98;—homogenized area
137 internal barriers
129—wall barriers
131—central opening All components of the disclosed novel electronic inhaler and their communication methods and technologies, materials, construction, sizes, cartridge sizes, shapes, cartridge shapes, cartridge selections and opening mechanisms, medication types and forms, etc. discussed above and/or shown in the drawings, are merely by way of example and are not considered limiting and other component(s) and their communication methods and technologies, materials, construction, sizes, cartridge sizes, shapes, cartridge shapes, cartridge selections and opening mechanisms, medication types and forms, etc. currently known and/or later developed can also be chosen and used and all are considered within the scope of the disclosure.

All measurements, amounts, frequencies, voltages, intensity amounts, sizes, shapes, percentages, configurations, securement or attachment mechanisms, dimensions, filtration mechanisms, sealing members, numbers, ranges, part locations, values, percentages, magnet types, sensor types, data readers, materials, orientations, methods of manufacture, etc. discussed above or shown in the drawing figures are merely by way of example and are not considered limiting and other measurements, amounts, frequencies, voltages, intensity amounts, sizes, shapes, percentages, configurations, securement or attachment mechanisms, dimensions, filtration mechanisms, sealing members, numbers, ranges, part locations, values, percentages, magnet types, system types, data readers, materials, orientations, methods of manufacture, etc. can be chosen and used and all are considered within the scope of the disclosure.

Furthermore, one or more features, components, characteristics, parts, uses, etc. discussed for one embodiment of the disclosure can also be used with another of the above discussed embodiments of the disclosure.

Additionally, for any numerical ranges discussed above, any combination of numbers within the range can be used to create a smaller size range from the outer limits of the numerical range specified and all such smaller ranges are also considered to be within the scope of the disclosure and also incorporated by reference without particularly listing each specific numerical value for the smaller ranges.

Unless feature(s), part(s), component(s), characteristic(s) or function(s) described in the specification or shown in the drawings for a claim element, claim step or claim term specifically appear in the claim with the claim element, claim step or claim term, then the inventor does not considered such feature(s), part(s), component(s), characteristic(s) or function(s) to be included for the claim element, claim step or claim term in the claim for examination purposes and when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the disclosure has been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein or shown in the drawings. Thus, a wide variety of alternatives, suggested by the teachings herein, can be practiced without departing from the spirit of the disclosure, and rights to such alternatives are particularly reserved and considered within the scope of the disclosure.

What is claimed is:
1. An electronic inhaler comprising:
a housing having a first end and a second end and defining a first medication passageway and a second medication passageway, the housing having an aperture at the first end and a homogenizing area at the second end and an internal passageway beginning at the aperture and terminating into the homogenizing area, the first medication passageway having a first end and a second end with the second end of the first medication passageway terminating into the homogenizing area and the second medication passageway having a first end and a second end with the second end of the second medication passageway terminating into the homogenizing area, a first end portion of the first medication passageway defining a first cartridge compartment and a first end portion of the second medication passageway defining a second cartridge compartment;
a first measuring reservoir compartment ("first MRC") disposed within an intermediate portion of the first medication passageway or defined by the intermediate portion of the first medication passageway;
a second measuring reservoir compartment ("second MRC") disposed within an intermediate portion of the second medication passageway or defined by the intermediate portion of the second medication passageway;
a first launch pad ("first LP) disposed at the second end of the first medication passageway, the first LP having an exit end in communication with the homogenizing area;
a second launch pad ("second LP") disposed at the second end of the second medication passageway, the second LP having an exit end in communication with the homogenizing area;
a microcontroller secured internally or externally to the housing for controlling operation of the electronic inhaler;
wherein the first cartridge compartment is adapted for receipt of a first cartridge and the second cartridge compartment is adapted for receipt of a second cartridge;
a first valve for controlling communication between the first MRC and the first cartridge when the first cartridge is disposed within the first cartridge component;

a second valve for controlling communication between the second MRC and the second cartridge when the second cartridge is disposed within the second cartridge compartment;
a third valve for controlling communication between the first MRC and the first LP and a fourth valve for controlling communication between the second MRC and the second LP.

2. The electronic inhaler of claim 1 wherein the microcontroller is configured to receive a medication or dosing schedule for a patient and controls a time of administering and an amount of medication dispensed through the first medication passageway or the second medication passageway based on the medication or dosing schedule.

3. The electronic inhaler of claim 1 further comprising a mouthpiece disposed at the second end of the housing, wherein the mouthpiece surrounds the homogenizing area when the mouthpiece is secured at the second end of the internal passageway.

4. The electronic inhaler of claim 3 wherein the mouthpiece is permanently secured to the housing.

5. The electronic inhaler of claim 3 wherein the mouthpiece is removably secured to the housing.

6. The electronic inhaler of claim 1 wherein the microcontroller is programmed to cause the first valve to be in an open position for a specific amount of time to permit a precise amount of content to flow from the first cartridge into the first MRC or to cause the second valve to be in an open position for a specific amount of time to permit a precise amount of content to flow from the second cartridge into the second MRC.

7. The electronic inhaler of claim 6 wherein the content from the first cartridge that the first cartridge compartment is configured to receive is a liquid medication and the content from the second cartridge that the second cartridge compartment is configured to receive is a dry powder medication.

8. The electronic inhaler of claim 3 wherein in use upon inhalation by a user air entering through the housing aperture and flowing through the internal passageway and received within the homogenizing area interacts with an amount of medication received into the homogenizing area from either the first LP or the second LP to create a torsional vortex.

9. The electronic inhaler of claim 3 further comprising one or more sensors disposed within the mouthpiece and in communication with the microcontroller to inform the microcontroller when a user inhales using the electronic inhaler.

10. The electronic inhaler of claim 1 wherein the microcontroller is programmed to cause either the third valve to be in an open position for a specific amount of time to permit a precise amount of content contained with the first MRC to flow to the first LP or to cause the fourth valve to be in an open position for a specific amount of time to permit a precise amount of content contained with the second MRC to flow to the second LP.

11. The electronic inhaler of claim 1 further comprising a first cartridge data reader disposed within the first cartridge compartment and a second cartridge data reader disposed within the second cartridge compartment.

12. An electronic inhaler comprising:
a housing having a first end and a second end and defining a first medication passageway and a second medication passageway, the housing having an aperture at the first end and a homogenizing area at the second end and an internal passageway beginning at the aperture and terminating into the homogenizing area, the first medication passageway having a first end and a second end with the second end of the first medication passageway terminating into the homogenizing area and the second medication passageway having a first end and a second end with the second end of the second medication passageway terminating into the homogenizing area, a first end portion of the first medication passageway defining a first cartridge compartment and a first end portion of the second medication passageway defining a second cartridge compartment;
a first measuring reservoir compartment ("first MRC") disposed within an intermediate portion of the first medication passageway or defined by the intermediate portion of the first medication passageway;
a second measuring reservoir compartment ("second MRC") disposed within an intermediate portion of the second medication passageway or defined by the intermediate portion of the second medication passageway;
a first launch pad ("first LP) disposed at the second end of the first medication passageway, the first LP having an exit end in communication with the homogenizing area;
a second launch pad ("second LP") disposed at the second end of the second medication passageway, the second LP having an exit end in communication with the homogenizing area;
a microcontroller secured internally or externally to the housing for controlling operation of the electronic inhaler;
wherein the first cartridge compartment is adapted for receipt of a first cartridge and the second cartridge compartment is adapted for receipt of a second cartridge;
a first barrier disposed within the homogenizing area in proximity to an exit end of the first LP and a second barrier disposed within the homogenizing area in proximity to an exit end of the second LP and a first wall disposed within the homogenizing area and a second wall disposed within the homogenizing area; the first barrier and the first wall defining a first substantially circular or oval shaped medication travel path and the second barrier and the second wall defining a second substantially circular or oval shaped medication travel path; the first wall and the second wall defining an exit aperture; wherein in use medication leaving the first LP travels through the first medication travel path before exiting the homogenizing area through the exit aperture or medication leaving the second LP travels through the second medication travel path before exiting the homogenizing area through the exit aperture.

13. An electronic inhaler comprising:
a housing having a first end and a second end and defining a first medication passageway and a second medication passageway, the housing having an aperture at the first end and a homogenizing area at the second end and an internal passageway beginning at the aperture and terminating into the homogenizing area, the first medication passageway having a first end and a second end with the second end of the first medication passageway terminating into the homogenizing area and the second medication passageway having a first end and a second end with the second end of the second medication passageway terminating into the homogenizing area, a first end portion of the first medication passageway defining a first cartridge compartment and a first end portion of the second medication passageway defining a second cartridge compartment;

a first measuring reservoir compartment ("first MRC") disposed within an intermediate portion of the first medication passageway or defined by the intermediate portion of the first medication passageway;
a second measuring reservoir compartment ("second MRC") disposed within an intermediate portion of the second medication passageway or defined by the intermediate portion of the second medication passageway;
a first launch pad ("first LP) disposed at the second end of the first medication passageway, the first LP having an exit end in communication with the homogenizing area;
a second launch pad ("second LP") disposed at the second end of the second medication passageway, the second LP having an exit end in communication with the homogenizing area; and
a microcontroller secured internally or externally to the housing for controlling operation of the electronic inhaler;
wherein the first cartridge compartment is adapted for receipt of a first cartridge and the second cartridge compartment is adapted for receipt of a second cartridge;
wherein an internal diameter of the first LP is greater in size at a first inlet end of the first LP as compared to a second exit end of the first LP and an internal diameter of the second LP is smaller in size at a first inlet end of the second LP as compared to a second exit end of the second LP.

14. An electronic inhaler comprising:
a housing having a first end and a second end and defining a first medication passageway and a second medication passageway, the housing having an aperture at the first end and a homogenizing area at the second end and an internal passageway beginning at the aperture and terminating into the homogenizing area, the first medication passageway having a first end and a second end with the second end of the first medication passageway terminating into the homogenizing area and the second medication passageway having a first end and a second end with the second end of the second medication passageway terminating into the homogenizing area, a first end portion of the first medication passageway defining a first cartridge compartment and a first end portion of the second medication passageway defining a second cartridge compartment;
a first measuring reservoir compartment ("first MRC") disposed within an intermediate portion of the first medication passageway or defined by the intermediate portion of the first medication passageway;
a second measuring reservoir compartment ("second MRC") disposed within an intermediate portion of the second medication passageway or defined by the intermediate portion of the second medication passageway;
a first launch pad ("first LP) disposed at the second end of the first medication passageway, the first LP having an exit end in communication with the homogenizing area;
a second launch pad ("second LP") disposed at the second end of the second medication passageway, the second LP having an exit end in communication with the homogenizing area;
a microcontroller secured internally or externally to the housing for controlling operation of the electronic inhaler;
wherein the first cartridge compartment is adapted for receipt of a first cartridge and the second cartridge compartment is adapted for receipt of a second cartridge; and
means for moving the second LP toward the second MRC when an amount of content is contained within the second MRC.

15. The electronic inhaler of claim 14 wherein the means for moving comprises an electromagnet disposed within the housing and in communication with the microcontroller; wherein the microcontroller is programmed to activate the electromagnet when the amount of content is contained within the second MRC, wherein the electromagnet is configured to create a pulling force on a spring secured to the second LP or directly on the second LP where the second LP is at least partially constructed from a magnetic material to cause the second LP to move inward toward the second MRC.

16. An electronic inhaler comprising:
a housing having a first end and a second end and defining a first medication passageway and a second medication passageway, the housing having an aperture at the first end and a homogenizing area at the second end and an internal passageway beginning at the aperture and terminating into the homogenizing area, the first medication passageway having a first end and a second end with the second end of the first medication passageway terminating into the homogenizing area and the second medication passageway having a first end and a second end with the second end of the second medication passageway terminating into the homogenizing area, a first end portion of the first medication passageway defining a first cartridge compartment and a first end portion of the second medication passageway defining a second cartridge compartment;
a first measuring reservoir compartment ("first MRC") disposed within an intermediate portion of the first medication passageway or defined by the intermediate portion of the first medication passageway;
a second measuring reservoir compartment ("second MRC") disposed within an intermediate portion of the second medication passageway or defined by the intermediate portion of the second medication passageway;
a first launch pad ("first LP) disposed at the second end of the first medication passageway, the first LP having an exit end in communication with the homogenizing area;
a second launch pad ("second LP") disposed at the second end of the second medication passageway, the second LP having an exit end in communication with the homogenizing area;
a microcontroller secured internally or externally to the housing for controlling operation of the electronic inhaler;
a mouthpiece disposed at the second end of the housing, wherein the mouthpiece surrounds the homogenizing area when the mouthpiece is secured at the second end of the internal passageway;
a first valve for controlling communication between the first MRC and the first cartridge when the first cartridge is disposed within the first cartridge component and a second valve for controlling communication between the second MRC and the second cartridge when the second cartridge is disposed within the second cartridge compartment;
a third valve for controlling communication between the first MRC and the first LP and a fourth valve for controlling communication between the second MRC and the second LP;

wherein the first cartridge compartment is adapted for receipt of a first cartridge and the second cartridge compartment is adapted for receipt of a second cartridge;

one or more sensors disposed within the mouthpiece and in communication with the microcontroller to inform the microcontroller when a user inhales using the electronic inhaler; and a first cartridge data reader disposed within the first cartridge compartment and a second cartridge data reader disposed within the second cartridge compartment;

wherein the microcontroller is configured to receive a medication or dosing schedule for a patient and controls a time of administering and an amount of medication dispensed through the first medication passageway or the second medication passageway based on the medication or dosing schedule;

wherein the microcontroller is programmed to cause the first valve to be in an open position for a specific amount of time to permit a precise amount of content to flow from the first cartridge into the first MRC or to cause the second valve to be in an open position for a specific amount of time to permit a precise amount of content to flow from the second cartridge into the second MRC;

wherein the microcontroller is programmed to cause either the third valve to be in an open position for a specific amount of time to permit a precise amount of content contained with the first MRC to flow to the first LP or to cause the fourth valve to be in an open position for a specific amount of time to permit a precise amount of content contained with the second MRC to flow to the second LP.

17. The electronic inhaler of claim 16 wherein the content from the first cartridge that the first cartridge compartment is configured to receive is a liquid medication and the content from the second cartridge that the second cartridge compartment is configured to receive is a dry powder medication.

18. The electronic inhaler of claim 16 wherein in use upon inhalation by a user air entering through the housing aperture and flowing through the internal passageway and received within the homogenizing area interacts with an amount of medication received into the homogenizing area from either the first LP or the second LP to create a torsional vortex.

19. The electronic inhaler of claim 16 further comprising a first barrier disposed within the homogenizing area in proximity to an exit end of the first LP and a second barrier disposed within the homogenizing area in proximity to an exit end of the second LP and a first wall disposed within the homogenizing area and a second wall disposed within the homogenizing area; the first barrier and the first wall defining a first substantially circular or oval shaped medication travel path and the second barrier and the second wall defining a second substantially circular or oval shaped medication travel path; the first wall and the second wall defining an exit aperture; wherein in use medication leaving the first LP travels through the first medication travel path before exiting the homogenizing area through the exit aperture or medication leaving the second LP travels through the second medication travel path before exiting the homogenizing area through the exit aperture.

20. The electronic inhaler of claim 16 wherein an internal diameter of the first LP is greater in size at a first inlet end of the first LP as compared to a second exit end of the first LP and an internal diameter of the second LP is smaller in size at a first inlet end of the second LP as compared to a second exit end of the second LP.

21. The electronic inhaler of claim 16 further comprising means for moving the second LP toward the second MRC when an amount of content is contained within the second MRC.

22. The electronic inhaler of claim 21 wherein the means for moving comprises an electromagnet disposed within the housing and in communication with the microcontroller; wherein the microcontroller is programmed to activate the electromagnet when the amount of content is contained within the second MRC, wherein the electromagnet is configured to create a pulling force on a spring secured to the second LP or directly on the second LP where the second LP is at least partially constructed from a magnetic material to cause the second LP to move inward toward the second MRC.

23. An electronic inhaler comprising:

a housing having a first end and a second end and defining a first medication passageway and a second medication passageway, the housing having an aperture at the first end and a homogenizing area at the second end and an internal passageway beginning at the aperture and terminating into the homogenizing area, the first medication passageway having a first end and a second end with the second end of the first medication passageway terminating into the homogenizing area and the second medication passageway having a first end and a second end with the second end of the second medication passageway terminating into the homogenizing area, a first end portion of the first medication passageway defining a first cartridge compartment and a first end portion of the second medication passageway defining a second cartridge compartment;

a first measuring reservoir compartment ("first MRC") disposed within an intermediate portion of the first medication passageway or defined by the intermediate portion of the first medication passageway;

a second measuring reservoir compartment ("second MRC") disposed within an intermediate portion of the second medication passageway or defined by the intermediate portion of the second medication passageway;

a first launch pad ("first LP) disposed at the second end of the first medication passageway, the first LP having an exit end in communication with the homogenizing area, an internal diameter of the first LP is greater in size at a first inlet end of the first LP as compared to a second exit end of the first LP;

a second launch pad ("second LP") disposed at the second end of the second medication passageway, the second LP having an exit end in communication with the homogenizing area, an internal diameter of the second LP is smaller in size at a first inlet end of the second LP as compared to a second exit end of the second LP;

a microcontroller secured internally or externally to the housing for controlling operation of the electronic inhaler;

a mouthpiece disposed at the second end of the housing, wherein the mouthpiece surrounds the homogenizing area when the mouthpiece is secured at the second end of the internal passageway;

a first valve for controlling communication between the first MRC and the first cartridge when the first cartridge is disposed within the first cartridge component and a second valve for controlling communication between the second MRC and the second cartridge when the second cartridge is disposed within the second cartridge compartment;

a third valve for controlling communication between the first MRC and the first LP and a fourth valve for controlling communication between the second MRC and the second LP;

wherein the first cartridge compartment is adapted for receipt of a first cartridge and the second cartridge compartment is adapted for receipt of a second cartridge;

one or more sensors disposed within the mouthpiece and in communication with the microcontroller to inform the microcontroller when a user inhales using the electronic inhaler;

a first cartridge data reader disposed within the first cartridge compartment and a second cartridge data reader disposed within the second cartridge compartment; and a vibrating apparatus associated with the second medication passageway;

wherein the microcontroller is configured to receive a medication or dosing schedule for a patient and controls a time of administering and an amount of medication dispensed through the first medication passageway or the second medication passageway based on the medication or dosing schedule;

wherein the microcontroller is programmed to cause the first valve to be in an open position for a specific amount of time to permit a precise amount of content of liquid medication to flow from the first cartridge into the first MRC or to cause the second valve to be in an open position for a specific amount of time to permit a precise amount of content of dry powder medication to flow from the second cartridge into the second MRC;

wherein the microcontroller is programmed to cause either the third valve to be in an open position for a specific amount of time to permit a precise amount of content of liquid medication contained with the first MRC to flow to the first LP or to cause the fourth valve to be in an open position for a specific amount of time to permit a precise amount of content of dry powder medication contained with the second MRC to flow to the second LP;

wherein in use upon inhalation by a user air entering through the housing aperture and flowing through the internal passageway and received within the homogenizing area interacts with an amount of medication received into the homogenizing area from either the first LP or the second LP to create a torsional vortex.

24. The electronic inhaler of claim 23 further comprising a first barrier disposed within the homogenizing area in proximity to an exit end of the first LP and a second barrier disposed within the homogenizing area in proximity to an exit end of the second LP and a first wall disposed within the homogenizing area and a second wall disposed within the homogenizing area; the first barrier and the first wall defining a first substantially circular or oval shaped medication travel path and the second barrier and the second wall defining a second substantially circular or oval shaped medication travel path; the first wall and the second wall defining an exit aperture; wherein in use medication leaving the first LP travels through the first medication travel path before exiting the homogenizing area through the exit aperture or medication leaving the second LP travels through the second medication travel path before exiting the homogenizing area through the exit aperture.

25. The electronic inhaler of claim 23 further comprising an electromagnet disposed within the housing and in communication with the microcontroller; wherein the microcontroller is programmed to activate the electromagnet when an amount of content is contained within the second MRC, wherein the electromagnet is configure to create a pulling force on a spring secured to the second LP or directly on the second LP where the second LP is at least partially constructed from a magnetic material to cause the second LP to move inward toward the second MRC.

\* \* \* \* \*